United States Patent [19]

Mori et al.

[11] Patent Number: 5,126,128
[45] Date of Patent: Jun. 30, 1992

[54] PERIPLANONE-B ANALOGUES AS WELL AS COCKROACH ATTRACTANT

[75] Inventors: Masataka Mori; Kentaro Okada; Kazuko Shimazaki; Tatsuji Chuman, all of Yokohama, Japan

[73] Assignee: Japan Tobacco Inc., Tokyo, Japan

[21] Appl. No.: 598,435

[22] Filed: Oct. 16, 1990

[30] Foreign Application Priority Data

Oct. 16, 1989 [JP] Japan ................... 1-266309

[51] Int. Cl.$^5$ ................ A01N 25/00; C07D 303/18
[52] U.S. Cl. ......................... 424/84; 549/332; 549/546; 549/215
[58] Field of Search ........... 424/84; 549/546, 332, 549/215

[56] References Cited

U.S. PATENT DOCUMENTS

| | | | |
|---|---|---|---|
| 4,639,532 | 1/1987 | Schreiber | 549/546 |
| 4,755,626 | 7/1988 | Mori et al. | 568/821 |
| 4,911,907 | 3/1990 | Shimamura et al. | 424/84 |
| 4,980,485 | 12/1990 | Mori et al. | 549/332 |

FOREIGN PATENT DOCUMENTS 3639941 6/1988 Fed. Rep. of Germany.
7118518 9/1967 Japan.

OTHER PUBLICATIONS

Persoons et al., Tetrahedron Letters, No. 24, pp. 2055-2058 (1976).
Greigger et al., Jounal of the American Chemical Society, 101:9, pp. 2493-2494 (1979).
Still, Journal of the American Chemical Society, 101:9, pp. 2495-2498 (1979).
Schreiber et al., J. Am. Chem. Soc., 106, pp. 4038-4039 (1984).
Hauptmann et al., Tetrahedron Letters, vol. 27, No. 12, pp. 1315-1318 (1986).
Kitahara et al., Tetrahedron Letters, vol. 27, No. 12, pp. 1343-1346 (1986).
Takahashi et al., J. Org. Chem., 51, pp. 3393-3394 (1986).
De Clercq et al., Tetrahedron Letters, vol. 29, No. 49, pp. 6501-6504 (1988).
Persoons et al., J. Chem. Ecol., 5, pp. 221-237 (1979).
Hauptmann et al., Tetrahedron Letters, vol. 27, No. 51, pp. 6189-6192 (1986).
Bowers et al., Nature, vol. 232, pp. 259-261 (1971).
Tahara et al., Agr. Biol. Chem., 39 (7), pp. 1517-1518 (1975).
Nishino et al., Appl. Ent. Zool., 12 (3), pp. 287-290 (1977).

Primary Examiner—Alan L. Rotman
Assistant Examiner—Amelia A. Owens
Attorney, Agent, or Firm—Birch, Stewart, Kolasch & Birch

[57] ABSTRACT

Periplanone-B analogue of (4E, 8R, 9R, 10R)-8,9-epoxy-5-methyl-10,10-methylene-oxy-4-cyclodecen-1-one, suitable as cockroach attractant can be prepared by reacting 6-methyl-2,6-cyclodecadien-1-one with a silylating reagent under the presence of a basic catalyst to form a silyldienol ether, reacting the resultant ether with an organic peracid to obtain (2Z, 6E)-10-hydroxy-6-methyl-2,6-cyclodecadien-1-one, reacting the resultant product with a peroxide under the presence of a basic catalyst after protecting hydroxy groups thereof with protection groups to obtain an epoxide, reacting the epoxide with chloromethyl lithium or dimethyl sulfonium methylide thereby introducing a spiroepoxy group and then removing the protection groups, to obtain (1S, 4E, 8R, 9R, 10S)-8,9-epoxy-5-methyl-10,10-methyleneoxy-4-cyclodecen-1-ol and, further, oxidizing the resultant product with a chromic acid type or dimethyl sulfoxide type oxidizing agents.

9 Claims, No Drawings

5,126,128

PERIPLANONE-B ANALOGUES AS WELL AS COCKROACH ATTRACTANT

BACKGROUND OF THE INVENTION

1. Field of the Invention

The present invention concerns a novel periplanone-B analogue used as biologically active material, in particular, as attractant for cockroaches, etc.

2. Description of the Prior Art

Cockroaches are typical insanitary and unpleasant pests which invade in various industrial places as well as domestic houses to give great damages. In view of the above, although various controlling methods have been used, use of insecticides suffer from restrictions since their habitats are closely related with human livings. In addition, effective control can not be obtained by conventional insect trapping means since cockroaches have a habit of hiding themselves in narrow gaps, etc. and have a strong reproducibility and they would be repeat infestation even after control.

In recent years, studies have been developed for pheromones of cockroaches and the study for using them to the control of cockroaches has been started. Pheromones are chemical substances secreted from insects for the preservation of species and it has been known that pheromones show potent activity such as attraction even in a very minute amount. Accordingly, it is considered that a pheromone can provide effective and non-toxic novel control means if it is used as an attractant for insect catching means.

By the way, periplanone-B is a compound having the structure represented by the following formula (B):

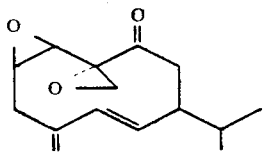

which is a major component of a sex pheromone secreted from female American cockroach (*Periplaneta americana*), which attracts male cockroaches to cause sexual excitation even in a amount of $10^{-6}-10^{-7}$ μg. The compound (B) was isolated and determined for the structure by Persoons, et al. (C. J. Persoons, et al., Tetrahedron Letters, 24, 2055 (1976)) and its stereochemistry was determined by Still, Nakanishi, et al (W. C. Still, J. Am. Chem. Soc., 101, 2493 (1979); K. Nakanishi, et al., J. Am. Chem. So., 101, 2495 (1979)).

The synthesizing process has been reported, in addition to the Still's method as described above, also by Schreiber, et al (S. L. Schreiber, et al., J. Am. Chem. Soc., 106, 4038 (1984)), Hauptmann, et al. (Hauptmann, et al., 27, 1315 (1986)), Kitahara, et al. (T. Kitahara, et al., Tetrahedron Lett., 27, 1343 (1986)), Takahashi, et al (T. Takahashi, et al., J. Org. Chem., 51, 3394 (1986)), De Clercq, et al., (P. J. De Clercq, et al., Tetrahedron Lett., 29, 6501 (1988)).

In addition, a minor pheromone component, periplanone-A is also known (C. J. Persoons, et al., J. Chem. Ecol., 5, 22 (1979); H. Hauptmann, et al., Tetrahedron Lett., 27, 6189 (1986)), and the structure has recently been determined (M. Mori, et al., J. Chem. Soc. Perkin Trans, 1, 1769 (1990)).

Other kinds of substances having sexual pheromone activity much weaker than that of natural pheromones, which are known as mimics, have also been found and there are known bornyl acetate (W. S. Bowers, et al., Nature, 232, 259 (1971)), germacrene-D (S. Takahashi, et al., Agric. Biol. Chem., 39, 1517 (1975)), verbenyl ester, verbanyl ester (C. Nishino, et al., Appl. Entomol. Zool., 12, 287 (1977)).

For applying the known pheromones and mimics as described above to the control of American cockroach (*Periplaneta americana*) there are the following problems.

Periplanone-B can be obtained only by 0.2 mg even when collected from 75,000 cockroaches and it is impossible to use extractants from insects as an attractant. Accordingly, it is necessary for the mass production by an organic synthesis process.

However, there are the following difficulties:

(1) Synthesis for 10-membered carbon rings as the fundamental skelton is difficult, for which no practical production process has yet been established, (2) Since the compound has many asymmetric carbon atoms and its stereoisomers show no activity, it requires a highly skillfull stereo-controlling method in view of synthesis.

(3) Since the compound has an unstable structure such as epoxy group or diene in the molecule, it is easily decomposed.

(4) Since existent synthetic processes require lengthy production steps because many functional groups have to be introduced in a stereoselective manner and many reactions such as organic metal reactions or cyclizing reactions requiring accurate condition settings are used, they are not practical.

In addition, since known pheromonally active substances (mimics), even powerful ones, have activity only to 1/1,000,000 of natural products, they have even not yet been put to practical use at present.

SUMMARY OF THE INVENTION

In view of the foregoing problems, the present inventors have made an earnest study with an aim of developing a practically useful pheromone derivative. As a result, we have obtained a knowledge based on the detailed analysis for the conformation of known active substances and the study on the structure-activity relationships that the conformation and steric coordination of oxygen-containing functional groups in the 10-membered ring are important for the development of the activity. Then, we have designed the present compound (A) having a structure in which isopropyl group and exomethylene group other than the functional carbon groups are removed from periplanone-B, that is, (4E, 8R, 9R, 10R)-8,9-epoxy-5-methyl-10,10-methyleneoxy-4-cyclodecen-1-one.

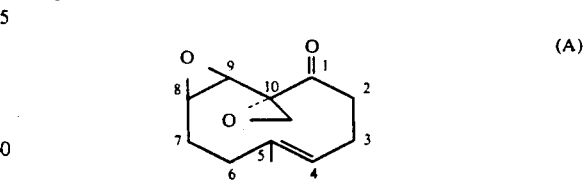

The compound (A) according to the present invention can be prepared by reacting 6-methyl-2,6-cyclodecadien-1-one with a silylating agent under the presence of a basic catalyst to form a silyldienol ether, reacting the resultant ether with an organic peracid to form (2Z, 6E)-10-hydroxy-6-methyl-2,6-cyclodecadien- 1-one, reacting it with a peroxide under the presence of a basic catalyst after protecting hydroxy groups thereof with protective groups to form an epoxide, reacting the epoxide with chloromethyl lithium or dimethyl sulfonium methylide, to thereby introducing a spiroepoxy groups, removing the protective groups to obtain (1S, 4E, 8R, 9R, 10S)-8,9-epoxy-5-methyl-10,10-methyleneoxy-4-cyclodecen-1-ol and, further, oxidizing the resultant product with a chromic acid type oxidizing agent or dimethylsufoxide type oxidizing agent.

The thus obtained compound (A) according to the present invention is a crystalline compound and has a steric arrangement and conformation identical with those of periplanone-B (B). Referring to the biological activity, it has an intense attracting and sexual exciting activity at an activity threshold value of $10^{-3}$ µg to male American cockroach (*Periplaneta americana*).

The starting material for preparing the compound (A) according to the present invention, that is, 6-methyl-2,6-cyclodecadien-1-one (compound (C)) is a known material easily obtained by a fragmentation reaction which is a method capable of forming a 10-membered ring which conveniently and in a large scale. For instance, it can be prepared by the method of Warton, et al. (J. Org. Chem., 36, 2932 (1971)).

The physicochemical properties of the compound (C) are as shown below:

Boiling point: 82°–82.5° C. (1.5 mmHg)
Refractive Index ($n_D^{24.5}$): 1.5148
IR (cm$^{-1}$): 3016(w), 2932(s), 2860(s), 1684(s), 1620(s), 1454(s), 1404(s), 1249(m), 1224(m), 1199(m), 1181(s), 1093(s), 942(s), 830(s)
$^1$H-NMR(300 MHz, CDCl$_3$, δ, ppm): 1.46(3H, J = 1.4 Hz), 1.89(2H, br), 1.95(2H, m), 2.11(2H, m, H-8), 2.26(2H, br.), 2.43(2H, br.), 4.78(1H, br. t, J = 6.5, H-7), 5.71(1H, dt, J = 11.6, 8.6 Hz, H-2), 6.29(1H, d, J = 11.6 Hz, H-1)
Molecular formula: C$_{11}$H$_{16}$O
Molecular weight: 164

The compound (A) according to the present invention can be synthesized starting from the compound (C) and by way of each of the following steps.

First step:

The compound (C) is at first treated with 1 to 5 molar equivalents, preferably, 1.1 to 1.5 molar equivalents of a strong base, for example, n-butyl lithium, lithium diisopropylamide and sodium hydride, preferably, lithium diisopropylamide in an inert gas stream such as anhydrous nitrogen or argon, in a solvent, for example, an ether type solvent such as diethyl ether or tetrahydrofuran, or hydrocarbon solvent such as hexane or toluene either alone or as a mixture, preferably, tetrahydrofuran, for 0.5 to 3 hours, preferably, one hour at a temperature lower than 0° C., preferably, from −20° to −40° C. to enolization.

Then, when 1 to 5 equi-molar amount, preferably, 1.1 to 2 molar equivalents of a silylating reagent, for example, trimethylsilyl chloride, triethylsilyl chloride or t-butyl-dimethylsilyl chloride, preferably, trimethylsilyl chloride is added and reacted for 0.5 to 2 hours and the reaction product is concentrated as it is under a reduced pressure, coarse silyl dienol ether is obtained. The coarse product is reacted with from 1 to 2 molar equivalents of an organic peracid, preferably, m-chloroperbenzoic acid using a hydrocarbon solvent, for example, n-hexane or chloroform, preferably, n-hexane for 0.5 to 2 hours at a temperature lower than 0° C., preferably, from −10° to −20° C. till the starting material is completely consumed, to obtain a hydroxyketone compound (D).

Second step:

Hydroxy group in the compound (D) obtained by the first step are brought into reaction with silyl type protecting reagent such as trimethylsilyl chloride, triethylsilyl chloride or t-butyldimethylsilyl chloride, acetal type protecting reagent such as ethyl vinyl ether, dihydropyrane or 2,2-dimethoxypropane, or ether type protecting reagent such as alkyl halide, to obtain a protected compound (E).

In this case, when triethylsilyl chloride is used, for example, as the protecting reagent, from 1 to 2 molar equivalents of the reagent is preferably reacted at a room temperature from 2 hours to one night by using pyridine as the solvent. In a case of using t-butyldimethylsilyl chloride, 1 to 3 molar equivalents of the reagent is preferably reacted at a room temperature or at 30°–60° C. from 2 hours to one night by using dimethylformamide as the solvent and imidazole as the catalyst. Further, in a case of using ethyl vinyl ether as the protecting reagent, a method of reacting 1.5 to 3 molar equivalents of the reagent at a room temperature from 2 hours to one night by using methylene chloride as the solvent can be utilized.

Third step:

The protected compound (E) obtained by the second step is added in an inert gas stream while using an ether type solvent such as diethyl ether or tetrahydrofuran into a mixture of 1 to 4 molar equivalents, preferably, 1.5 molar equivalents of an organic peroxide, for example, t-butyl peroxide and 1 to 4 molar equivalents, preferably, 1.4 equi-molar amount of a strong base, for example, sodium hydride, potassium hydride and Triton-B, preferably, potassium hydride at a temperature lower than 10° C., preferably, from −10° to −20° C., and reacted as they are for 0.5 to 4 hours, to obtain an epoxy ketone (compound (F)).

Fourth step:

The compound (F) obtained by the third step is brought into reaction with a mixture of 1 to 4 molar equivalents, preferably, 1.5 molar equivalents of chlromethyl iodoxide or trimethyl sulfonium iodide and from 1 to 4 molar equivalents of a strong base, preferably, n-butyl lithium, methyl lithium, lithium diisopropylamide or sodium hydride, in an inert gas stream while using, for example, an ether type solvent such as diethyl ether or tetrahydrofuran alone or as a mixture thereof with dimethylsulfoxide, at a temperature, for example, from −40° to 10° C. and from 0.5 to 2 hours, thereby introducing spiroepoxy groups to obtain a bisepoxide (compound (G)).

Fifth step:

Since hydroxy groups are protected in the compound (G) obtained by the fourth step, the thus protected hydroxy groups are deprotected by using an appropriate deprotecting agent, for example, tetra-n-butylammonium fluoride, hydrogen fluoride or potassium fluoride if the protective group is the silyl type protective group, hydrogen chloride, sulfuric acid, p-toluene sulfonic acid, pyridinium-p-toluene sulfonate or acetic acid if the protection group is the acetal type protective group, or hydrogen halide or other acid catalyst if the protection group is the ether type protection group respectively, to obtain a hydroxy bisepoxide (compound (H)).

Sixth Step:

The compound (H) obtained by the fifth step is oxidized by using 1 to 10 molar equivalents, preferably, 2 molar equivalents, based on the substrate, of a chromic acid type oxidizing agent, for example, pyridinium chlorochromate, pyridinium chlorochromate-molecular sieves 3A, pyridinium dichromate or other oxidizing agents such as dimethylsulfoxideoxalyl chloride or dimethylsulfide-N-chlorosuccinimide, preferably, pyridinium chlorochromate-molecular sieves 3A in a solvent, for example, methylene chloride or chloroform, preferably, methylene chloride at a temperature lower than the room temperature, preferably, at 0° C. for 1 to 3 hours, to obtain a compound (A) according to the present invention.

EXAMPLE

The present invention will now be explained more specifically referring to examples.

First Step:

A solution of lithium diisopropylamide was prepared from 2.6 ml of diisopropylamine and 2.8 ml of 1.6M n-butyl lithium in an argon gas stream at −10° C. using anhydrous tetrahydrofuran as a solvent, to which 2.0 g of the compound (C), i.e., 6-methyl-2,6-cyclodecadien-1-one was added dropwise under stirring at −20° C. for 3 min. After stirring the mixture for 15 min, 2.4 ml of trimethyl silyl chloride was added altogether and the temperature was elevated to a room temperature under stirring. The reaction mixture was directly concentrated under a reduced pressure to obtain coarse silyldienol ether. 2.6 g of m-chloroperbenzoic acid was suspended in 100 ml of hexane and stirred at −15° C. for 30 min, to which the above-mentioned coarse product was added and stirred vigorously at −15° to −20° C. for 1.5 hr. After the reaction was completed, the reaction mixture was filtered under suction, and precipitates were washed with hexane and the liquid filtrate and the washing solution were combined and concentrated under a reduced pressure. The resultant oily product was purified on a column chromatography using 50 g of silica gel to obtain 1.4 g (64% yield) of (2Z, 6E)-10-hydroxy-6-methyl-2,6-cyclodecadien-1-one (compound (D)).

The physicochemical properties of the compound are as shown below.

Nature: waxy

Refractive index ($n_D^{24.5}$)m: 1.5267

IR (cm$^{-1}$): 3454(br, s), 3016(w), 2924(s), 2860(s), 1680(s), 1620(s), 1454(s), 1390(s), 1257(s), 1191(s), 1071(s), 772(s)

$^1$H-NMR(300 MHz, CDCl$_3$, δ, ppm): 1.37(3H, s, CH$_3$), 1.50(1H, m, H-5), 2.05(1H, m, H-9), 2.1–2.3(2H, m, H-4,5), 2.35(1H, m, J-9), 2.79(1H, m, H-3), 2.35(1H, m, H-9), 3.98(1H, br. s., OH), 4.16(1H, br. dt, J=4.3, 2.5 Hz, H-10), 4.63(1H, br. d, J=11.8 Hz, H-7), 5.87(1H, ddd, J=11.6, 9.7, 7.4 Hz, H-3), 6.30(1H, dd, J=11.6, 1.1 Hz, H-2)

Molecular formula: C$_{11}$H$_{16}$O$_2$

Second Step:

The compound (D) obtained by the first step was dissolved by 604 mg into 6 ml of anhydrous pyridine, to which 0.85 ml of triethylsilyl chloride was added dropwise and reacted at room temperature for 2 hr. After the reaction was completed, pyridine was removed by concentration under a reduced pressure and the residue was extracted twice with n-hexane with addition of water. After washing the organic phase with water and a saturated solution of aqueous sodium chloride, it was dried with anhydrous magnesium sulfate and the solvent was removed. The resultant coarse product was subjected to column chromatography using 20 g of silica gel, to obtain 725 mg (72% yield) of (2Z, 6E)-10-triethylsilyloxy-6-methyl-2,6-cyclodecadien-1-one (compound (E)).

The physicochemical properties of the compound are as shown below.

Nature: waxy

Refractive index ($n_D^{24.5}$): 1.4937

IR (cm$^{-1}$): 3020(w), 2920(s), 2880(s), 1688(s), 1620(s), 1458(s), 1093(s), 1015(s), 837(s), 729(s)

$^1$H-NMR(300 MHz, CDCl$_3$, δ, ppm): 0.63(6H, q, J=8.0 Hz, Si(C$_2$H$_5$)$_3$), 0.97(9H, t, J=8.0 Hz, Si(C$_2$H$_5$)$_3$), 1.44(3H, s, CH$_3$), 1.7–2.8(8H, br), 4.07(1H, br. s, H-10), 4.9(1H, br., H-7), 5.8(1H, br. m, H-3), 6.6(1H, br., H-2)

Molecular formula: C$_{17}$H$_{30}$O$_2$Si

Third Step:

In an argon gas stream, 75 mg of potassium hydride removed with mineral oils was suspended in 10 ml of anhydrous tetrahydrofuran and under stirring at −15° C., 0.8 ml of toluene solution containing t-butylhydroperoxide was added and stirred for 30 min, to which 1 ml solution of tetrahydrofuran containing 500 mg of the compound (E) obtained in the second step described above was added dropwise and reacted at −15° to −20° C. for 2 hr. After the reaction was completed, water and a saturated solution of aqueous ammonium chloride were added and extracted for three times with methylene chloride. The aqueous phase was washed with a saturated solution of aqueous sodium chloride and then dried over magnesium sulfate, and the solvent was removed after filtration to obtain a coarse product. The product was subjected to column chromatography using 15 g of neutral aluminum (activity II), to obtain 295 mg (56% yield) of (2S, 5E, 9R, 10R)-9,10-epoxy-6-methyl-2-triethysilyloxy-5-cyclodecen-1-one (compound (F)).

The physicochemical properties of the compound are as shown below.

Nature: waxy

Refractive index ($n_D^{24.5}$): 1.4913

IR (cm$^{-1}$): 2958(s), 2880(s), 1717(s), 1458(s), 1419(s), 12 43(m), 1114(s), 1017(s), 845(s), 745(s)

$^1$H-NMR(300 MHz, CDCl$_3$, δ, ppm): 0.69(6H, q, J=8.0 Hz, Si(C$_2$H$_5$)$_3$), 1.01(9H, t, J=8.0, Si(C$_2$H$_5$)$_3$), 1.43(1H, m, H-3), 1.58(3H, s, CH$_3$), 1.81(1H, m, H-4), 1.9–2.0(2H, m, H-7,8), 2.1–2.2(2H, m, H-3',4'), −2.3(2H, m, H-7',8'), 3.23(1H, ddd, J=10.3, 4.8, 3.0 Hz, H-2), 4.27(1H, br. d, J=6.2 Hz, H-6), 4.28(1H, d, J=4.8 Hz, H-1), 4.95(1H, br., H-6)

Molecular formula: C$_{17}$H$_{30}$O$_3$Si

Fourth Step:

(a) In an argon gas stream, 280 mg of the compound (F) obtained by the third step described above and 0.1 ml of chloromethyl iodide were dissolved in 3 ml of anhydrous tetrahydrofuran and cooled to −78° C. 1 ml of an ether solution containing 1.2M methyl lithium was dropped to the solution under stirring and the temperature was elevated to a room temperature after stirring for 2 min. After the reaction was completed, an saturated solution aqueous of ammonium chloride was added and extracted twice with diethyl ether. After washing the organic phase with water and a saturated solution of aqueous sodium chloride, it was dried with magnesium sulfate, filtered and then the solvent was removed. The product was subjected to column chromatography using 10 g of neutral silica gel to obtain 248 mg (85% yield) of (1S, 4E, 8R, 9R, 10R)-8,9-epoxy-5-methyl-10,10-methyleneoxy-4-chclodecen-1-ol-triethylsilyl ether (compound (G)).

The physicochemical properties of the compound are as shown below.

Nature: waxy

IR (cm$^{-1}$): 3062(w), 2918(s), 2880(s), 1460(s), 1296(m), 1270(m), 1241(s), 1083(s), 1006(s), 946(s), 806(s), 745(s)

$^1$H-NMR(300 MHz, CDCl$_3$, δ, ppm): 0.58(6H, q, J=8.1 Hz, Si(C$_2$H$_5$)$_3$), 0.95(9H, t, J=8.1 Hz, Si(C$_2$H$_5$)$_3$), 1.70(3H, s, CH$_3$), 1.7-2.1(8H, m), 2.35(1H, d, J=6.2 Hz, spiroepoxy), 2.76(1H, d, J=6.2 Hz, spiroepoxy), 2.99(1H, dt, J=10.5, 3.9 Hz, H-8), 3.25(1H, dd, J=10.8, 4.5 Hz, H-1), 3.38(1H, d, J=3.9 Hz, H-9), 5.17(1H, br, H-4)

Molecular formula: C$_{18}$H$_{32}$O$_3$Si (b) The compound (G) was synthesized from the compound (F), separately from the above, as shown below.

In an argon gas stream, 204 mg of trimethylsulfonium iodide was suspended in 3 ml of anhydrous tetrahydrofuran and cooled to −15° C. Then, 0.65 ml of a hexane solution containing 1.6M n-butyl lithium was added dropwise under stirring and, after stirring for 10 min, the temperature was elevated once to a room temperature to form a homogenous solution. The solution was again cooled to −10° C., to which 78 mg of the compound (F) was added dropwise and reacted for 1 hr.

After the reaction was completed, a saturated solution of aqueous ammonium chloride was added and extracted twice with diethyl ether. After washing the organic phase with water and a saturated solution of aqueous sodium chloride, it was dried with magnesium sulfate, filtered and then removed with the solvent. The product was subjected to silica gel column chromatography, to obtain 39 mg (48% yield) of a pure compound (G).

Fifth Step:

The compound (G) obtained by the fourth step described above was dissolved by 140 mg into 0.5 ml of anhydrous tetrahydrofuran, to which 0.5 ml of 1M-tetrabutylammonium fluoride was added and stirred at 25° C. for 30 min. Diethyl ether was added and extracted three times. After washing the extracted organic phase with a saturated solution of sodium aqueous chloride, it was dried with magnesium sulfate, filtered and then removed with the solvent. The product was subjected to column chromatography using 5 g of neutral silica gel, to obtain 80 mg of crystals (90% yield) of (1S, 4E, 8R, 9R, 10S)-8,9-epoxy-5-methyl-10,10-methyleneoxy-4-cyclodecen-1-ol (compound (H)).

The physicochemical properties of the compound are as shown below.

Melting point: 83°–85° C.

IR (cm$^{-1}$): 3460(br, s), 3060(w), 2930(s), 2858(s), 1460(s), 1435(s), 1272(m), 1156(m), 1048(s), 1009(s), 936(s), 897(s), 837(s), 702(s)

$^1$H-NMR(300 MHz, CDCl$_3$, δ, ppm): 1.71(3H, s, CH$_3$), 1.7-1.9(3H, m), 1.9-2.2(5H, m), 2.46(1H, d, J=6.1 Hz, spiroepoxy), 2.79(1H, d, J=6.1 Hz, spiroepoxy), 3.03(1H, dt, J=10.6, 4.0 Hz, H-8), 3.23(1H, dd, J=11.4, 4.5 Hz, H-1), 3.31(1H, d, J=4.0 Hz, H-9), 5.14(1H, br, H-6)

Molecular formula: C$_{12}$H$_{18}$O$_3$

Sixth Step

In anhydrous methylene chloride, 150 mg of pyridinium chlorochromate and 350 mg of molecular sieve-3A were vigorously stirred, to which 76 mg of the compound (H) was added and oxidized at 0° C. for 1 hr. Diethyl ether was added to the reaction mixture and insoluble matters were removed by filtration in a short column of florisil and the solvent was removed to obtain a coarse product. The coarse product was subjected to column chromatography using 5 g of neutral silica gel, to obtain 55 mg (73% yield) of pure (4E, 8R, 9R, 10R)-8,9-epoxy-5-methyl-10,10-methyleneoxy-4-cyclodecen-1-one (compound (A)).

The physicochemical properties of the compound are as shown below.

Melting point: 66.6°–68° C.

IR (cm$^{-1}$): 2992(m), 2932(m), 2868(m), 1709(s), 1450(m), 1332(m), 1267(m), 1046(m), 1017(m), 922(s), 835(s), 787(m), 704(m), 571(s)

$^1$H-NMR(300 MHz, CDCl$_3$, δ, ppm): 1.62(3H, d, J=1.4 Hz, CH$_3$), 1.78(1H, m, H-6), 1.87(1H, m, H-7), 2.01(1H, ddd, J=12.8, 5.4, 2.7 Hz, H-2), 2.17(1H, m, H-7'), 2.23(1H, br., H-3), 2.43(1H, br., H-6'), 2.63(1H, m, H-3'), 2.72(1H, d, J=5.7 Hz, spiroepoxy), 2.91(1H, ddd, J=12.5, 10.0, 3.0 Hz, H-2'), 2.97(1H, d, J=5.7 Hz, spiroepoxy), 2.98(1H, dt, J=10.7, 3.8 Hz, H-8), 3.82(1H, J=3.8, 0.4 Hz, H-9), 5.49(1H, m, H-4)

Molecular formula: C$_{12}$H$_{16}$O$_3$

TEST EXAMPLE

Filter paper was laid on the bottom of a glass vessel sized 12.5 cm length, 18.5 cm width and 29 cm height with its upper surface being opened, and a black line was drawn along the center part of the filter paper so as to bisect the lateral length. Then, a wooden box sized 5.8 cm length, 7.7 cm height and 12.5 cm width and partitioned in the direction of the width into 7 compartments was attached to the glass vessel laterally in connection with an opening of 7.7 cm height formed to the lower portion of the longitudinal side of the vessel to constitute a shelter.

A diluted solution of a test specimen in hexane was introduced together with an air stream at a rate of 200 ml/min from a glass nozzle attached to the upper portion of the test vessel.

Five unmated 4–12 week aged male American cockroach (*Periplaneta americana*) after imaginal ecdysis were set free in a testing vessel under red light. When left as they were for 10 min, all of them entered into the shelter and stood still. In this state, the diluted solution of the test specimen in hexane was introduced and (1) the number of times that cockroaches getting out of the shelter and passed across the black line at the bottom of the vessel within one minute after the introduction of the test specimen was counted and it was defined as the attracting activity and (2) the number of cockroaches, among five, that showed wing-raising as the typical mating behavior was counted and it was defined as the sexual excitation activity.

In this test, germacrene-D known as an effective pheromone mimic (control product (X)) and the compound (A) according to the present invention were introduced, as the test specimens, into the testing vessel such that their amounts was varied or changed by 10 times, and measurement was conducted by three times an each introduced amount, to determine the relationship between the amount of introduction and the activity. The results are as shown in Table 1 and it has been found that intense attracting and sexual excitation activity are shown at an activity threshold of $10^{-5}$ μg against male American cockroach (*Periplaneta americana*).

TABLE 1

| No. | Compound | Amount introduced μg | Attracting activity | Sexual excitation activity |
|---|---|---|---|---|
| 1 | (A) | 1 | 68 | 5/5 |
| 2 | " | $10^{-1}$ | 54 | 5/5 |
| 3 | " | $10^{-2}$ | 40 | 5/5 |
| 4 | " | $10^{-3}$ | 27 | 3/5 |
| 5 | " | $10^{-4}$ | 2 | 1/5 |
| 6 | " | $10^{-5}$ | 0 | 0/5 |
| 7* | (X) | 10 | 17 | 3/5 |
| 8* | " | 1 | 1 | 0/5 |
| 9* | " | $10^{-1}$ | 0 | 0/5 |
| 10* | hexane (solvent) alone | | 0 | 0/5 |

* control experiment

The threshold activity of pheromone mimic for American cockroach (*Periplaneta americana*) known at present is about 1 μg even with the strongest one, and the compound (A) according to the present invention has an activity greater by more than 1000 times as compared therewith. Further, since the structure of the compound (A) is simple, the production steps can be shortened remarkably as compared with those for natural products. Furthermore, since the compound contains not so many unstable groups and asymmetric carbon atoms, the molecule is highly stable and there is not trouble for the steric control. In addition, since a convenient fragmentation reaction can be utilized for the formation of the 10-membered ring which is a key reaction to the synthesis of the periplanone derivative, this is more advantageous than the prior art process.

The compound (A) according to the present invention has excellent properties as described above and is extremely useful for the control of cockroaches.

What is claimed is:

1. (4E, 8R, 9R, 10R)-8,9-epoxy-5-methyl-10,10-methylene-oxy-4-cyclodecen-1-one.

2. (2S, 5E, 9R, 10R)-9,10-epoxy-6-methyl-2-triethylsilyloxy-5-cyclodecen-1-one.

3. (1S, 4E, 8R, 9R, 10R)-8,9-epoxy-5-methyl-10,10-methyleneoxy-4-cyclodecen-1-ol-triethylsilyl ether.

4. (1S, 4E, 8R, 9R, 10S)-8,9-epoxy-5-methyl-10,10-methyleneoxy-4-cyclodecen-1-ol.

5. An attractant for cockroaches comprising:
   as an effective ingredient, (4E, 8R, 9R, 10R)-8,9-epoxy-5-methyl-10,10-methyleneoxy-4-cyclodecen-1-one; and
   a carrier.

6. The attractant of claim 4, wherein the carrier is paper.

7. The attractant of claim 4, wherein the carrier is hexane.

8. A method for attracting cockroaches, comprising:
   applying an effective cockroach attracting amount of the compound (4E, 8R, 9R, 10R)-8,9-epoxy-5-methyl-10,10-methylene-oxy-4-cyclodecen-1-one to an area having cockroaches.

9. The method of claim 7, wherein the compound is applied to paper.

* * * * *